(12) United States Patent
Neumann

(10) Patent No.: US 12,430,177 B1
(45) Date of Patent: Sep. 30, 2025

(54) APPARATUS AND METHOD FOR RESOURCE GUIDANCE

(71) Applicant: KPN INNOVATIONS LLC, Lakewood, CO (US)

(72) Inventor: Kenneth Neumann, Lakewood, CO (US)

(73) Assignee: KPN INNOVATIONS LLC, Lakewood, CO (US)

( * ) Notice: Subject to any disclaimer, the term of this patent is extended or adjusted under 35 U.S.C. 154(b) by 0 days.

(21) Appl. No.: 18/989,893

(22) Filed: Dec. 20, 2024

(51) Int. Cl.
*G06F 9/46* (2006.01)
*G06F 9/50* (2006.01)
*G16H 20/60* (2018.01)

(52) U.S. Cl.
CPC ........... *G06F 9/5033* (2013.01); *G16H 20/60* (2018.01)

(58) Field of Classification Search
CPC .............................. G06F 9/5033; G16H 20/60
See application file for complete search history.

*Primary Examiner* — Gregory A Kessler
(74) *Attorney, Agent, or Firm* — Caldwell Intellectual Property Law

(57) ABSTRACT

An apparatus for resource guidance, wherein the apparatus comprises at least a processor; and a memory communicatively connected to the at least a processor, wherein the memory containing instructions configuring the at least a processor to receive a request for a resource containing a desired allocation; identify a first nourishment provider for a first resource; label the first resource as a function of the desired allocation; identify a second nourishment provider for a second resource; label the second resource as a function of the first nourishment resource and the desired allocation; receive a depot label from the first nourishment provider and the second nourishment provider; aggregate the first resource and the second resource as a function of the depot label; and generate resource guidance using the depot label.

18 Claims, 6 Drawing Sheets

APPARATUS AND METHOD FOR RESOURCE GUIDANCE

FIELD OF THE INVENTION

The present invention generally relates to the field of resource aggregation. In particular, the present invention is directed to an apparatus and method for resource guidance.

BACKGROUND

Resource aggregation is a vital process for provisioning resources. However, existing methods suffer from inaccuracy in guidance and lack accuracy.

SUMMARY OF THE DISCLOSURE

In an aspect, an apparatus for resource guidance, wherein the apparatus comprises at least a processor; and a memory communicatively connected to the at least a processor, wherein the memory containing instructions configuring the at least a processor to receive a request for a resource containing a desired allocation; identify a first nourishment provider for a first resource; label the first resource as a function of the desired allocation; identify a second nourishment provider for a second resource; label the second resource as a function of the first nourishment resource and the desired allocation; receive a depot label from the first nourishment provider and the second nourishment provider; aggregate the first resource and the second resource as a function of the depot label; and generate resource guidance using the depot label.

In yet another non-limiting aspect, A method for resource guidance, the method comprising receiving, by at least a processor, a request for a resource containing a desired allocation; identifying, by the at least a processor, a first nourishment provider for a first resource; labeling, by the at least a processor, the first resource as a function of the desired allocation; identifying, by the at least a processor, a second nourishment provider for a second resource; labeling, by the at least a processor, the second resource as a function of the first nourishment resource and the desired allocation; receiving, by the at least a processor, a depot label from the first nourishment provider and the second nourishment provider; aggregating, by the at least a processor, the first resource and the second resource as a function of the depot label; and generating, by the at least a processor, resource guidance using the depot label.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Figure 1:
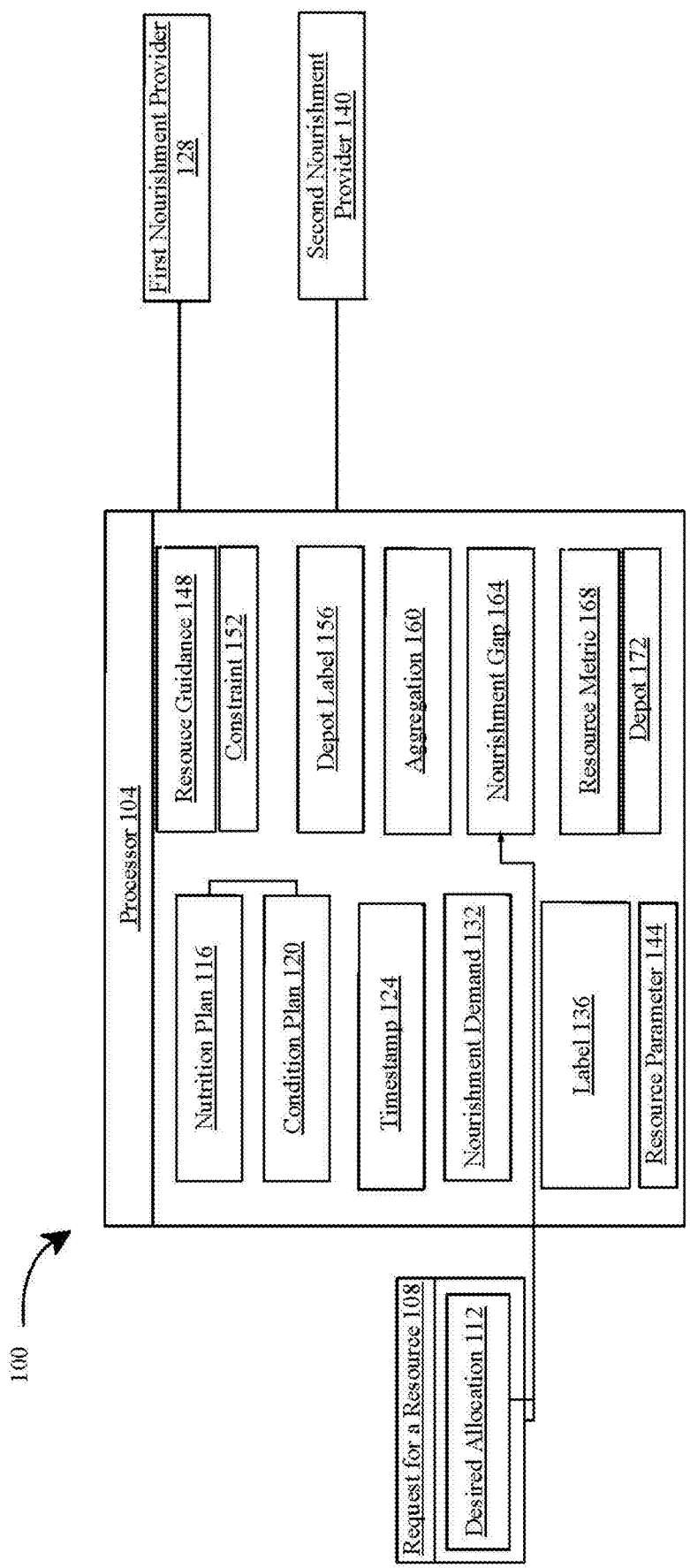
FIG. 1 is an illustration of an exemplary embodiment of an apparatus for resource guidance.

Referring now to FIG. 1, an exemplary embodiment of an apparatus 100 for generating a refreshment hash is illustrated. Processor 104 may include any computing device as described in this disclosure, including without limitation a microcontroller, microprocessor 104, digital signal processor 104 (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of system 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor 104 cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, as used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, apparatus, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example, and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, without limitation, via a bus or other facility for intercommunication between elements of a computing device. Communicative connecting may also include indirect connections via, for example, and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, processor 104 is configured to receive a request for a resource 108 containing a desired allocation 112. A "request for a resource 108" as used in this disclosure, is any order for a product. A product may include any consumable and/or non-consumable item. A consumable may include any food and/or beverage available for consumption by a human being. A consumable may include a recipe, a meal such as: breakfast; lunch; dinner; and/or a snack. A consumable may include an ingredient such as for example a fruit, a vegetable, a grain, a cereal, meat, poultry, fish, seafood, dairy products, eggs, legumes, beans, nuts, seeds, oils, fats, baked goods, snack, confectionary, prepared food, plant based alternatives, fermented foods, herbs, spices, beverages, any combination thereof and the like. For instance and without limitation, a consumable may include a combination of one or more of the following apples, bananas, berries, oranges, mangoes, grapes, spinach, carrots, potatoes, broccoli, tomatoes, lettuce, brown rice, quinoa, oats, barley, millet, whole wheat, white rice, white bread, pasta, beef, pork, lamb, chicken, turkey, duck, salmon, tuna, cod, tilapia, sardines, shrimp, crab, lobster, clams, oysters, milk, cheese, yogurt, butter, cream, chicken eggs, duck eggs, quail eggs, lentils, chickpeas, kidney beans, black beans, peas, soybeans, almonds, walnuts, cashews, peanuts, chia seeds, flax seeds, sunflower seeds, olive oil, coconut oil, butter, ghee, lard, margarine, bread, cakes, pastries, cookies, pies, chips, popcorn, chocolate, candy, ice cream, pizza, burgers, sandwiches, soups, salads, sushi, tofu, tempeh, seitan, plant-based burgers, almond milk, soy milk, coconut yogurt, yogurt, kimchi, sauerkraut, kombucha, pickles, basil, rosemary, turmeric, ginger, cinnamon, garlic, pepper, water, juices, tea, coffee, smoothies, soda, wine, beer, and the like. A consumable may range in terms of nutrition, taste, preparation method, quantity, ingredient quality, and the like. A consumable may include a beverage including any liquid prepared as a drink. A beverage may include for example water, juice, soft drinks, coffee, smoothie, tea, milk, alcoholic beverages such as wine, beer, and spirits. A beverage may be consumed hot or cold, with varying flavors and ingredients. A consumable may include a pre-made meal, a meal kit, a meal with pre-packaged ingredients to cook at home, a collection of ingredients to make a particular meal or recipe, and/or any combination thereof.

With continued reference to FIG. 1, a product may include a non-consumable. A "non-consumable" as used in this disclosure, is any product, ingredient, merchandise, additive, component, element, article, durable good, furniture, appliance, electronic, clothing, tool, book, household good, personal care items, digital media, streaming media, and the like. A non-consumable may include any product available for purchase and/or delivery.

With continued reference to FIG. 1, a request for a resource 108 contains a desired allocation 112. A "desired allocation 112" as used in this disclosure is any information pertaining to a request for a resource 108. Information may include user demographic information such as name, gender, address, date of birth, payment method, contact information of purchaser and/or recipient, tracking information, special instructions, order status, delivery instructions and contact information, income level, occupation, education level, marital status, purchase history and the like. A desired allocation 112 may include information pertaining to a purchase including a timeline of how quickly or slowly a user may be seeking to receive a request for a resource 108. For instance and without limitation, a user may indicate that a request for a resource 108 such as a meal may be desirable to be delivered within 45 minutes whereas a request for a resource 108 such as a new quart of paint may be desirable to be delivered within 2 weeks.

With continued reference to FIG. 1, a desired allocation 112 may include information measurements of biological extraction data. Biological extraction data includes any biological extraction data found in U.S. patent application Ser. No. 16/372,512, filed on Apr. 2, 2019, and entitled "METHODS AND SYSTEMS FOR UTILIZING DIAGNOSTICS FOR INFORMED VIBRANT CONSTITUTIONAL GUIDANCE," the entirety of which is incorporated herein by reference. A desired allocation 112 may include information relating to a phenotypic cluster. A "phenotypic cluster" as used in this disclosure, is a group of one or more phenotypes located within a specified geographical location. A "geographical location" as used in this disclosure is any boundary defined by a map, GPS, RFID, wi-fi, cellular data and the like. For example, a geographical location may include a specific location such as a shopping center, or a restaurant. A geographical location may include a location such as Denver, Colorado, a neighborhood such as Back Bay in Boston, Massachusetts, a zip code such as 02114, a town such as Savannah, Geogia, and the like. A phenotypic cluster may contain a prevalence factor. A "prevalence factor" as used in this disclosure, is any proportion of a population within a geographical location that have a specific characteristic, condition, and/or phenotype at a given time. A prevalence factor may be expressed as a percentage or fraction such as the prevalence of influenza within a geographical location may be 20%. A phenotypic cluster within a geographical location may specify for example a prevalence of individuals with Type Two Diabetes Mellitus located within Atlanta, Georgia. A phenotype and/or phenotype cluster may include any phenotype and/or phenotype cluster as described in U.S. patent application Ser. No. 18/090,411 filed on Dec. 28, 2022 and entitled "APPARATUS AND METHOD FOR SCORING A NUTRIENT" and U.S. patent application Ser. No. 17/976,329 filed on Oct. 28, 2022 and entitled "APPARATUS AND METHOD FOR GENERATING AN INGREDIENT 124 CHAIN" both of which are incorporated by reference in their entirety.

With continued reference to FIG. 1, a desired allocation 112 may include a nutrition plan 116. A "nutrition plan 116" as used in this disclosure, is a guide outlining dietary guidelines and food intake recommendations designed to help a user achieve particular health and/or fitness goals. A nutrition plan 116 may include recommendations of nutrients such as carbohydrates, proteins, fats, vitamins and minerals based upon a user's needs, preferences, biological extraction measurements, preferences, lifestyle and/or health conditions. A nutrition plan 116 may include recommendations of caloric intake indicating daily energy needs based on age, gender, weight, height, activity level, and/or health objectives. A nutrition plan 116 may include recommendations of macronutrients including a proportion of carbohydrates, proteins, and fats tailored to a person's goals. A nutrition plan 116 may include recommendations of meal frequency and timing including guidance on how many meals or snacks to eat each day and optimal time of consumption based on optimal nutrient absorption and energy levels. A nutrition plan 116 may include recommendations of food choices and restrictions including specific recommendations on which foods to include and which to avoid or limit. A nutrition plan 116 may include recommendations of hydration including guidelines for daily fluid intake to support metabolism, digestion, and overall health. A nutrition plan 116 may include recommendations of supplementation including any suggestions for vitamins and minerals if dietary sources alone are insufficient to meet nutrient requirements. A nutrition plan 116 may be generated using a machine learning process, including any machine learning process as described below in more detail. A nutrition plan 116 may be generated based on any biological extraction data and/or any phenotypic cluster data as described above in more detail. A nutrition plan 116 may be generated based upon input from one or more healthcare providers including for example any dietitians, nutritionists, health coaches, physicians, nurses, and the like. A nutrition plan and/or generation of a nutrition plan may include any nutrition plan and/or alimentary instruction set U.S. patent application Ser. No. 16/372,512, filed on Apr. 2, 2019, and entitled "METHODS AND SYSTEMS FOR UTILIZING DIAGNOSTICS FOR INFORMED VIBRANT CONSTITUTIONAL GUIDANCE," the entirety of which is incorporated herein by reference.

With continued reference to FIG. 1, desired allocation 112 includes a condition plan 120. A "condition plan 120" as used in this disclosure, is a guide outlining health recommendations to assist a user in achieving and maintaining optimal physical, mental, and/or emotional well-being. A condition plan 120 may include aspects such as preventative care, lifestyle modifications, treatment strategies, and/or regular assessments to manage, maintain and/or improve a health status. A condition plan 120 may indicate a user's health goals including for example specific objectives such as improving fitness, managing weight, reducing stress, controlling a chronic condition, reducing the risk of developing a chronic condition and the like. A condition plan 120 may include guidance on preventative care including for example recommendations on regular screenings, vaccinations, and/or preventative check-ups to detect potential health issues early. A condition plan 120 may include one or more recommendations for diet and nutrition, including any information contained within a nutrition plan 116 as described above in more detail. A condition plan 120 may include recommendations for physical activity, including recommendations for exercise types, frequency, and intensity tailored to individual goals and physical abilities. A condition plan 120 may include lifestyle modifications including adjustments in habits such as sleep, alcohol intake, smoking cessation, and other behaviors that impact health. A condition plan 120 may include monitoring and assessments to include regular health check-ins, tracking progress and making adjustments as needed to stay on course. A condition plan 120 may be generated using artificial intelligence, as described below in more detail. A condition plan 120 may be generated based on input from healthcare providers, wellness coaches, health insurers, and the like.

With continued reference to FIG. 1, desired allocation 112 includes a timestamp 124. A "timestamp 124" as used in this disclosure, is any temporal data relating to a request for a resource 108 and/or a desired allocation 112. Temporal data may include information such as the date and time when a request for a resource 108 and/or desired allocation 112 is generated. Temporal data may indicate the precise hour, minute, second, and/or millisecond Temporal data may include information pertaining to a delivery timeline. Temporal data may include delivery instructions including any specific instructions for a resource upon arrival. For instance and without limitation, temporal data may indicate that a request for a resource 108 was generated by a user at 4:12 pm ET on Oct. 23, 2024. In yet another non-limiting example, temporal data may indicate that a request for a resource 108 containing a desired allocation 112 indicating a purchase of Wild Alaskan Salmon may contain delivery instructions for the salmon to be left on a front porch upon delivery in a spot with extra shade coverage.

With continued reference to FIG. 1, processor 104 identifies a first nourishment provider 128 for a first resource. A "nourishment provider" as used in this disclosure, is any supplier of a resource. A supplier may include any individual and/or entity who supplies resources, any ingredient of a resource, and/or component thereof. A nourishment provider may include an individual, an entity, a storefront, a shop owner, an e-commerce business, a boutique, a market, a retailer, an outlet, an emporium, a warehouse, a mart, an establishment, a showroom, a restaurant, a café, a bistro, a diner, an eatery, a brasserie, a grill, a cantina, a trattoria, a pizzeria, a buffet, a steakhouse, a tavern, a gastropub and the like. A nourishment provider may include any establishment that offers resources, any ingredient of a resource, and/or any component thereof for sale. For instance and without limitation, a nourishment provider may include a restaurant that offers Mediterranean meals and beverages. In yet another non-limiting example, a nourishment provider may include an online general retailer such as Amazon.com, eBay.com, Walmart.com and the like. In yet another non-limiting example a nourishment provider may include an online electronic retailer such as Bestbuy.com, Apple.com, and/or Newegg.com. In yet another non-limiting example, a nourishment provider may include an online electronic grocery store such as Instacart.com, FreshDirect.com, and/or ThriveMarket.com and the like. In yet another non-limiting example, a nourishment provider may include an online meal delivery service such as DoorDash.com, UberEats.com, Grubhub.com, and/or Postmates.com. In yet another non-limiting example, a nourishment provider may include a meal kit delivery service such as BlueApron.com, HelloFresh.com, HomeChef.com, and/or GreenChef.com.

With continued reference to FIG. 1, processor 104 parses the request for a resource 108 to identify a nourishment demand 132. "Parsing" as used in this disclosure, is any process of analyzing language including any string of symbols, code, and/or text to extract structured information and/or to understand its meaning based on a set of rules. Parsing may include syntax analysis including checking the structure of input data contained within a request for a resource 108 and comparing it to a specific syntax or grammar. Parsing may include data extraction including breaking down information contained with a request for a resource 108 into smaller data formats and/or components that can be understood and processed. For instance and without limitation, processor 104 may break down a date string such as 2024 Nov. 14 into year, month, and day parts. Parsing may include natural language processing including breaking down sentences and/or phrases such as language contained within a request for a resource 108 to understand and identify grammar, semantics, and/or parts of speech. Parsing may include the use of code parsing, HTML parsing, and/or log parsing.

With continued reference to FIG. 1, parsing may include a program automatically generated by processor 104 recognition to produce associations between one or more significant terms extracted from request for a resource 108 and detect associations, including without limitation mathematical associations, between such significant terms. Associations between language elements, where language elements include for purposes herein extracted significant terms, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted significant term indicates a given category of semantic meaning. As a further example, statistical correlations and/or mathematical associations may include probabilistic formulas or relationships indicating a positive and/or negative association between at least an extracted significant term and/or a given semantic relationship; positive or negative indication may include an indication that a given document is or is not indicating a category semantic relationship. Whether a phrase, sentence, word, or other textual element in request for a resource 108 constitutes a positive or negative indicator may be determined, in an embodiment, by mathematical associations between detected significant terms, comparisons to phrases and/or words indicating positive and/or negative indicators that are stored in memory at computing device, or the like.

Still referring to FIG. 1, processor 104 may generate the language processing program and/or parsing recognition by any suitable method, including without limitation a natural language processing classification algorithm; language processing model may include a natural language process classification model, for instance as generated by training neural network, that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between semantic elements such as terms, phrases, tokens, etc. There may be a finite number of categories to which an extracted word may pertain; an HMM inference algorithm, such as the forward-backward algorithm or the Viterbi algorithm, may be used to estimate the most likely discrete state given a word or sequence of words. Processor 104 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

In an embodiment, and still referring to FIG. 1, processor 104 may train neural network using multi-task learning. As used herein, multi-task learning (MTL) is a subfield of machine learning in which multiple learning tasks are solved at the same time, while exploiting commonalities and differences across tasks. This may result in improved learning efficiency and prediction accuracy for the task-specific models, when compared to training models separately.

With continued reference to FIG. 1, a "nourishment demand 132" as used in this disclosure, is data relating to a user's nutritional requirements. Nutritional requirements may include any information pertaining to any amounts and/or types of nutrients a person needs to maintain health, support growth, achieve a health goal, prevent disease, treat disease, maintain optimal health and wellness, and the like. Nutritional demand may specify particular quantities of essential nutrients, such as vitamins, minerals, essential amino acids, essential fatty acids, carbohydrates, proteins, fats, and the like. Nutritional demand may be customized based on factors such as age whereby infants, children, adults, and/or the elderly may have different nutritional needs. Nutritional demand may be customized based on gender, as men and women may have different nutrient requirements. Nutritional demand may be customized based on physical activity level whereby active individuals may require more calories and protein. Nutritional demand may be customized based on health conditions as certain health conditions may require specific dietary adjustments. Nutritional demand may be customized based on recommended dietary allowances such as those provided from health organizations such as the Institute of Medicine (IOM) and World Health Organization (WHO). Nutritional demand may be customized based on energy requirements including factors such as daily calorie needs, basal metabolic rate (BMR) and physical activity. Nutritional demand may be customized based on information pertaining to a user's biological extraction and/or phenotypic cluster. Nutritional demand may include any recommendations and/or specifications as described above in reference to a nutrition plan 116. Nutritional demand may be generated using a machine learning process, including any machine learning process as described herein.

With continued reference to FIG. 1, a user with a biological extraction that contains a Hemoglobin A1C with a level of 5.9% indicating prediabetes may contain a nourishment demand 132 indicating a recommendation for each meal to contain no more than 30 grams per meal. In yet another non-limiting example, a phenotypic cluster for pregnant women may include a nourishment demand 132 suggesting 27 milligrams of iron for pregnant women. Nourishment demand 132 may be generated based on health provider input including for example any recommendations and/or suggestions generated by general practitioners, family medicine physicians, internists, pediatricians, cardiologists, dermatologists, endocrinologists, orthopedic surgeons, neurologists, oncologists, registered nurses, nurse practitioners, licensed practical nurses, psychiatrists, psychologists, licensed clinical social workers, counselors, therapists, physical therapists, occupational therapists, speech language pathologists, dietitians, nutritionists, chiropractors, acupuncturats, massage therapists, naturopathic doctors, homeopaths, aromatherapists, reiki practitioners, herbalists, hypnotherapists, traditional medicine practitioners, energy healers, detox specialists, shamanic healers, tai chi practitioners, qigong practitioners, and the like. Nourishment demand 132 may be generated based on user response. A user response may indicate a dietary preference such as I don't like tomatoes, or I dislike onion. A user response may indicate dietary intolerance including any non-immune system reaction to foods or ingredients that cause digestive discomfort or other symptoms. For example, dietary intolerance may include but is not limited to lactose intolerance, gluten sensitivity, fructose intolerance, histamine intolerance, food additives, and the like. A user response may indicate a dietary allergy including any immune system response to a specific protein that the body mistakenly identifies as harmful. For example, a dietary allergy may include but is not limited to peanuts, tree nuts, shellfish, fish, milk, eggs, wheat, soy, and the like.

With continued reference to FIG. 1, processor 104 locates first nourishment provider 128 using nourishment demand 132 and resources. "Locating nourishment provider" as used in this disclosure, is any process of determining or identifying a nourishment provider able fulfill a request for a resource 108. Fulfilling a request for a resource 108 may include being able to provide any items and/or products contained within a request for a resource 108, including any desired allocation 112. In an embodiment, fulfilling a request for a resource 108 may include partially fulfilling a request for a resource 108 and/or partially fulfilling any desired allocation 112. In an embodiment, fulfilling a request for a resource 108 may include modifying a request for a resource 108 and/or any desired allocation 112. In an embodiment, fulfilling a request for a resource 108 may include canceling and/or delaying a request for a resource 108. For instance, and without limitation, a request for a resource 108 containing a menu item consisting of Greek chicken with hummus, tomatoes, and cucumber may be fulfilled when the menu item is confirmed to be able to be prepared and delivered by 3 pm by a first nourishment provider 128. In yet another non-limiting example, a request for a resource 108 containing an order for organic powdered matcha to be delivered by 4 pm PT may be fulfilled when a first nourishment provider 128 is located who is the only nourishment provider who has the organic powdered match in stock but it only able to get the powdered matcha delivered by 4:30 pm PT. In yet another non-limiting example, a nourishment provider may be located when a nourishment provider is able to provide a glass water container that is BPA free and also free of heavy metals and ensure delivery of the item within 4 days.

With continued reference to FIG. 1, processor 104 labels the first resource as a function of the desired allocation 112. A "label 136" as used in this disclosure is any information and/or data relating to the first resource and/or the desired allocation 112. A label 136 may include information about the first resource itself, including any ingredients and/or nutritional information about a resource such as a meal or snack. A label 136 may include information relating to storage conditions of a resource. For example, a resource that contains a meal comprising a chef's salad may contain a label 136 indicating that the resource needs to remain refrigerated and be shipped and/or delivered with cold packs to maintain temperature between 32-50 degrees Fahrenheit. A label 136 may include information relating to a desired allocation 112, including expected delivery time and/or date to a user. For example, a label 136 may indicate that a resource is expected to be delivered to a user by 5:00 pm ET on Tuesday March 25th. A label 136 may include information relating to one or more other resources that may be aggregated and delivered with the first resource. For example, a desired allocation 112 may indicate that a user has placed an order for three resources that are to be aggregated and delivered to a user by 11:00 am ET on Friday November 15th. A label 136 may include a barcode containing machine-readable code in the form of numbers and a pattern of parallel lines of varying widths or a grid pattern such as a QR code. The barcode may be utilized to store information that can be retrieved by scanning, including any information relating to a request for a resource 108 and/or a desired allocation 112. A barcode may include a 1D barcode and/or a 2D barcode. For example, a label 136 containing a barcode may indicate that a first resource is going to be aggregated with six other resources and that all six resources will be initially delivered to a sorting facility to be aggregated and then delivered at one.

With continued reference to FIG. 1, processor 104 identifies a second nourishment provider 140 for a second resource. A "second nourishment provider 140" as used in this disclosure, is any supplier of a resource. In an embodiment, a second nourishment provider 140 may be the same as a first nourishment provider 128. In an embodiment, a second nourishment provider 140 may be different than a first nourishment provider 128. In an embodiment, a request for a resource 108 may contain multiple requests for multiple different resources. For instance and without limitation, a request for a resource 108 placed by a user may contain a first request for a lunch meal, a second request for a dinner meal, and a third request for a handful of nonperishable food items to restock the user's pantry with. In yet another non-limiting example, a request for a resource 108 may be generated for a household with multiple family members and may include a first request for a first member of a household, a second request for a second member of a household, and a third request for a third member of a household. In yet another non-limiting example, a request for a resource 108 may be generated for an office with multiple officer members intending to order lunch together and may include a first request for a first officer worker, a second request for a second officer worker, and a third request for a third office worker.

With continued reference to FIG. 1, processor 104 receives a resource parameter 144 for a first nourishment parameter. A "resource parameter 144" as used in this disclosure, is any specification, requirement, standard, and/or customization relating to a request for a resource 108. A resource parameter 144 may include any allergies such as a request for an ingredient that is free of any peanut containing ingredients for a user with a peanut allergy. A resource parameter 144 may include any preparation specifications such as a request for a resource 108 prepared without the use of any seed oils. In yet another non-limiting example, a resource parameter 144 may include a request for a meal to be prepared in a dedicated gluten free kitchen for a user with Celiac disease. In yet another non-limiting example, a resource parameter 144 may include a request for a nourishment provider to package a resource in plastic-free packaging. In yet another non-limiting example, a resource parameter 144 may specify a certain quantity of nutrients that a user is seeking to obtain from a resource, such as a meal containing a minimum of 10 milligrams of iron for a user with iron deficiency anemia. In an embodiment, information pertaining to a resource parameter 144 may be generated based on a user's biological extraction information and/or phenotypic cluster information. For instance and without limitation, a user with a biological extraction indicating a disease such as rheumatoid arthritis may have a resource parameter 144 that specifies a minimum of 0.5 grams of omega three fatty acids in each meal. A resource parameter 144 may be generated based on a user's personal beliefs and practices. For example, a user may have preferences surrounding organic produce, grass fed and finished meats, toxin free household items, toxin free beauty products, environmental awareness, ethical choices, holistic health, connection with nature, waste reduction, avoidance of additives such as artificial colors, flavors, preservatives and the like. In such an instance, a user with a preference for toxin free beauty products may have a resource parameter 144 be generated that indicates a preference for all resources to be packaged in recycled non-toxic materials.

With continued reference to FIG. 1, processor 104 trains a machine learning process using training data correlating resource parameter 144 to resource guidance 148. Processor 104 computes resource guidance 148 as a function of the resource parameter 144 and the trained machine learning process. "Resource guidance 148" as used in this disclosure, is any instructions for delivery of a request for a resource 108. Instructions may include a delivery timeframe of when a request for a resource 108 is expected to be delivered. Instructions may include a delivery and/or completion timeframe when a first nourishment provider 128 and a second nourishment provider 140 may complete each resource and be ready for pickup. In some instances, a first resource and a second resource may each be delivered separately to a central location and from the central location be delivered to an end user. In some instances, a first resource may be picked up for delivery first, a second resource may be picked up for delivery second by the same delivery drive and then both may be delivered by the same driver to the user. In some instances, different drivers may collect and/or deliver resources. Resource guidance 148 may include route guidance, including instructions pertaining to delivery route for resources to arrive on time to specified locations of users. Processor 104 may optimize routes by calculating routes based on factors such as distance, traffic, delivery time windows, multiple stops and the like. Resource guidance 148 may include navigation technology using tools with global positioning system (GPS) to pinpoint locations and delivery. Resource guidance 148 may include audio and visual cues providing step by step guidance and updates based on real-time traffic updates, construction, road closures, accidents, and the like. Resource guidance 148 may include geofencing including alerts when approaching delivery zones or entering a specific service area. Resource guidance 148 may include drop-off instructions including notes where resources should be left at a physical location such as "leave at the back door" or "call upon arrival." Resource guidance 148 may include delivery time estimates including updated arrival times factoring in live conditions. Resource guidance 148 may include batch delivery such as multiple deliveries with routes optimized to reduce overall travel time and reduce impacts on the environment. Resource guidance 148 may include route history including repeated routes that may be saved due to frequent visits for quicker navigation. Resource guidance 148 may include real-time communication features such as a masked phone number or chat feature to communicate between delivery personnel, users, and/or processor 104. Resource guidance 148 may include live tracking for both delivery personnel and users. Resource guidance 148 may include delivery confirmation such as location specific photos when a request for a resource 108 is delivered to a user and/or delivered to any batching and/or depot 172 for packaging along the way. Resource guidance 148 may include precise delivery points on a map such as "by the lobby" or "at the mailroom." Resource guidance 148 may include driver adjustments based on route experiences to provide feedback about addresses or obstacles, thereby improving future navigation accuracy. Resource guidance 148 may include machine learning to improve routing, predicting high-traffic times, or suggesting shortcuts based on historical data.

With continued reference to FIG. 1, processor 104 is configured to identify a constraint 152 within the resource guidance 148. A "constraint 152" as used in this disclosure, is any factor that impacts resource guidance 148. Factors may include weather issues, visibility issues such as fog or heavy precipitation that may slow traffic, transportation delays due to traffic congestion, vehicle issues, air or rail delays, logistical challenges such as high volume periods, incorrect information, route optimization errors and the like. A constraint 152 may include package issues such as customs delays, lost packages, oversized packages, human error such as sorting mistakes, delivery attempt failure, and the like. A constraint 152 may include external factors such as strikes or labor shortages, global events such as pandemics or natural disasters, legal restrictions such as regulations around certain goods or products, customer related-issues such as unavailable recipients, changes in delivery addresses, systemic delays such as backlogs, carrier delays, miscommunication such as incomplete updates, missed notifications, and the like. A constraint 152 may include an obstacle such as traffic or a closed road. A constraint 152 may include a factor that arises during delivery, such as a delivery vehicle breakdown or driver who gets lost. A constraint 152 may include a factor such as a delayed completion time to prepare a resource by a nourishment provider. A constraint 152 may include conditions on the roads due to weather conditions such as rain, snow, ice, a storm and the like that may affect travel.

With continued reference to FIG. 1, processor 104 updates resource guidance 148 as a function of a constraint 152. Updating resource guidance 148 may include any change to resource guidance 148. For instance and without limitation, a constraint 152 indicating heavy traffic in a particular geofenced location may cause processor 104 to update resource guidance 148 to contain a new delivery time that is 45 minutes later than expected, due to the heavy traffic. In yet another non-limiting example, a constraint 152 indicating a nourishment provider has run out of organic chicken may cause resource guidance 148 to be updated to indicate that organic turkey has been substituted in a resource. In yet another non-limiting example, a constraint 152 indicating that a delivery person traveling on a bicycle has a breakdown may cause a resource guidance 148 to be updated to indicate that an energy efficient delivery is unavailable and the resource will not be delivered by a car instead.

With continued reference to FIG. 1, processor 104 label 136 second resource as a function of the first nourishment resource and the desired allocation 112. Labeling 136 second resource may be performed utilizing any methodology as described above in more detail. Labeling 136 second resource may be performed utilizing desired allocation 112. For instance and without limitation, a desired allocation 112 that indicates a user preference for gluten free meals and ingredients may be utilized by processor 104 to label 136 second resource as gluten free after confirming resource contained within second resource is actually gluten free. This may be performed for example, by confirming with second nourishment provider 140. In yet another non-limiting example, a desired allocation 112 that indicates a user prefers recycled plastic free packaging may cause processor 104 to generate a label 136 for first resource and second resource indicating that each has respectively been contained in plastic free packaging.

With continued reference to FIG. 1, processor 104 receives a depot label 156 from the first nourishment provider 128 and second nourishment provider 140. A "depot label 156" as used in this disclosure, is information pertaining to aggregation 160 of a resource. A depot label 156 may indicate any particulars as to collection and consolidation of a resource. This may include for example, order processing (e.g. item, destination, and priority), and if item will be collected and sent to a warehouse or fulfillment center. A depot label 156 may indicate any picking and packaging such as where goods are to be selected from inventory if applicable. A depot label 156 may include information pertaining to batching orders, such as multiple resources contained within a request for a resource 108 and/or orders headed to the same region or requiring similar transport conditions. A depot label 156 may include sorting instructions including primary sorting instructions at a nourishment provider including sorting instructions containing data relating to a destination, carrier, and/or priority. Sorting instructions may include automated sorting systems including any instructions for the use of conveyor belts, scanners, and/or robotics to quickly sort one or more resources. A depot label 156 may include any information relating to regional aggregation 160 including data relating to transportation to a hub, secondary sorting, and/or palletization. For instance and without limitation, resources may be transported from nourishment providers to any regional and/or national hubs where they may be further aggregated and assembled for delivery to the same users. Various secondary sorting techniques may be employed and resources bound for the same or close-by destinations may be grouped and loaded together to streamline the process. A depot label 156 may include information pertaining to local distribution, including any transfer to local centers, driver allocation and final aggregation 160. For instance and without limitation, resources may arrive at local, geofenced locations for final distribution before delivery. In yet another non-limiting example, multiple resources may be bundled together and assigned to specific delivery personnel based on available delivery personnel in particular delivery zones and within specified timeframes. A depot label 156 may include information relating to specialized aggregation 160 resources including multi-stop shipments whereby resources for multiple stops may be aggregated within the same delivery route. A depot label 156 may include information pertaining to any perishable and/or temperature sensitive resources including any that require refrigeration such as food items and/or medications which may be grouped and stored in temperature controlled conditions. A depot label 156 may include information pertaining to oversized deliveries, including any large or bulky resources that may be aggregated separately due to special handling requirements. A depot label 156 may include information pertaining to real-time adjustments including any dynamic re-sorting. For instance and without limitation, a resource that is delayed or has an unexpected route change due to weather may be rerouted to one more hubs. A depot label 156 may include any information relating to load balancing, including for example during high-volume periods when extra drivers or routes may be added to handle the increased volume.

With continued reference to FIG. 1, processor 104 aggregates the first resource and the second resource as a function of the depot label 156. "Aggregation 160" of one or more resources as used in this disclosure, is any processing of resources for delivery to an end user. Processing may include any process such as collection and consolidation whereby when an order is first placed, information contained within a request for a resource 108 are shared with resource providers, and instructions for aggregation 160 are contained within depot label 156. Aggregation 160 may include any picking and packaging of resources including picking up resources from nourishment providers, packaging them for transport, and labeling 136 them with barcodes and/or QR codes for tracking. Aggregation 160 may include any process of batching orders whereby multiple resources contained within a request for a resource 108 are grouped together for delivery. For instance and without limitation, aggregation 160 may include a process whereby a first resource, a second resource, and a third resource all being delivered to the same user and address are grouped, batched together, and packaged for delivery. Aggregation 160 may include any sorting that may occur of resources, including for example sorting that occurs based upon factors such as destination, delivery method, and/or priority of delivery. Aggregation 160 may include any process of regional aggregation 160, including any transportation to hubs, secondary sorting, and/or palletization. For instance and without limitation, aggregation 160 may take into account delivery vehicle and weight of delivery. For example, resources available for delivery by bicycle may be restricted based upon factors such as dimensions, weight, and length of delivery route whereby resources available for delivery by a compact car may have specific requirements, and resources available for delivery by SUV may have other specific requirements pertaining to size, weight, dimensions, and the like. Aggregation 160 may include any process of flagging, identifying, and/or labeling 136 resources which require particular delivery conditions, such as perishable goods that require refrigeration within a specified temperature range. Aggregation 160 may include any process of route optimization including any process intended to determine the most efficient way to group and delivery resources. Aggregation 160 may include any process that happens at any local distribution centers, regional hubs, and/or directly at fulfillment centers.

With continued reference to FIG. 1, processor 104 is configured to locate a nourishment gap 164 associated with a first nourishment provider 128 and identify a third nourishment provide for the nourishment gap. A "nourishment gap" as used in this disclosure, is any difference between nutrients a user consumes and nutrients the user needs for optimal health. A nourishment gap 164 may occur when a user requests a resource for a meal, snack, and/or food item that lacks sufficient vitamins, minerals, and/or other essential nutrients required for proper bodily functions. A nourishment gap 164 may be caused by poor dietary choices, restricted diets, health conditions, increased needs due to certain life stages, economic and/or accessibility issues and the like. For instance and without limitation, a user who is pregnant may require additional nutrients than a user of the same age and sex who isn't pregnant. In yet another non-limiting example, a child experiencing a growth spurt may require additional nutrients. In yet another non-limiting example, a user with a chronic digestive disorder such as ulcerative colitis who is unable to absorb fat soluble nutrients may have a nourishment gap 164 indicating low levels of vitamins and minerals such as Vitamin A, Vitamin D, Vitamin E, Vitamin K, calcium, phosphorus, and magnesium.

With continued reference to FIG. 1, processor 104 may analyze nutrients contained in any resources to identify nourishment gaps associated with nourishment providers and thus locate other nourishment providers who may be able to provide nourishment to fill in those gaps. For instance and without limitation, a first resource that contains a food item containing sunflower butter for a user with dyslipidemia may cause processor 104 to locate a third nourishment provider to supply a dose of Omega-3 fatty acids that aid in balancing the user's omega 3-fatty acid profile and don't further exacerbate the user's dyslipidemia. In some instances, processor 104 may locate a third nourishment provider for the nourishment gap 164 to aid in absorption of a first resource. For example, a first resource that contains a food item containing steak for a user with anemia may cause processor 104 to identify a third nourishment provider who can supply sauteed red bell peppers to be consumed together with the steak as red bell peppers are high in Vitamin C and aid in iron absorption. In some instances, processor 104 may locate a third nourishment provider for the nourishment gap 164 to lessen damage caused by consumption of a first resource. For example, a first resource that contains a food item containing fried chicken may cause processor 104 to identify a third nourishment provider who can supply antioxidant rich foods to counteract health impacts of free radicals contained in fried foods such as berries, oranges, grapes, spinach, kale, and broccoli. These may be combined to create an antioxidant rich smoothie for a user to consume after fried chicken.

With continued reference to FIG. 1, a nourishment gap 164 may be identified using a biological extraction and/or phenotypic cluster information. For instance, and without limitation, a biological extraction that reflects a user with leaky gut may cause processor 104 to identify nutrients to soothe the gut and promote gut barrier integrity such as aloe vera juice, green tea, polyphenol rich olive oil and foods rich in Vitamin A such as sweet potatoes and carrots. In yet another non-limiting example, a phenotypic cluster that indicates one or more users labeled 136 as "prediabetic" may cause processor 104 to identify nutrients aimed at reducing fasting blood glucose levels such as leafy greens, almonds, avocados, whole grains, oats, fatty fish, and the like. In yet another non-limiting example, a phenotypic cluster that indicates one or more users labeled 136 as "pregnant" may cause processor 104 to identify nutrients aimed at supporting growth and development of a fetus including leafy greens, citrus fruits, berries, avocado, lean proteins such as chicken turkey, and lean beef, while limiting nutrients such as high-mercury fish, raw or undercooked meats, unpasteurized dairy, and excess caffeine.

With continued reference to FIG. 1, processor 104 is configured to determine a resource metric 168 between the first nourishment provider 128 and a depot 172 and select the first nourishment provider 128 as a function of the resource metric 168. A "resource metric 168" as used in this disclosure is any measurement of preparation and travel time for a resource to arrive at a depot 172 for aggregation 160 and delivery to a user. A "depot 172" as used in this disclosure is any location where resources may be aggregated and/or collected for delivery. A depot 172 may include a facility where resources may be stored temporarily before distribution and/or delivery. A resource metric 168 may indicate, for example, the travel time from a first nourishment provider 128 to a depot 172. A resource metric 168 may indicate, for example, the preparation time for a resource to get prepared and/or arrive at a nourishment provider. For example, a resource such as a meal consisting of a vegan lasagna made with zucchini noodles may take 6 hours of time for a nourishment provider to cook and prepared, and an additional 2 hours for the lasagna to be cooled and transported to the depot 172. In yet another non-limiting example, a resource such as a chemical free sunscreen may take 48 hours for a nourishment provider to get in stock, and then an additional 72 hours for the chemical free sunscreen to be transported to the depot 172.

With continued reference to FIG. 1, processor 104 may select a nourishment provider using a resource metric 168. For example, processor 104 may identify a first potential nourishment provider with a resource metric 168 of 3 days and a second potential nourishment provider with a resource metric 168 of 2.5 hours. In such an instance, processor 104 may assign the first potential nourishment provider to a first request for a resource 108 containing a desired allocation 112 of 1 week, whereby the second potential nourishment provider may be assigned to a second request for a resource 108 containing a desired allocation 112 of 4 hours. In some instances, processor 104 may utilize desired allocation 112s to match requests for resources to nourishment providers who are able to complete orders within desired timeframes specified in requests for resources.

With continued reference to FIG. 1, processor 104 is configured to review the first resource and the second resource and calculate a provider fulfillment score for the first resource and the second resource as a function of the desired allocation 112 and the reviewed first resource and the reviewed second resource. Reviewing the first resource and the second resource may include determining nutrient delivery and quantity contained within the first resource and the second resource. Reviewing the first resource and the second resource may also include determining ingredient quality, standards, and source used within a resource.

Reviewing the first resource and the second resource may include determining a refreshment preparation style. A "refreshment preparation style" as used in this disclosure, is any preparation method utilized to create and/or prepare a resource. A refreshment preparation style may impact flavor, texture, and overall quality of a resource. A refreshment preparation style may indicate for example, chopping, dicing, slicing, mincing, grating, peeling, marinating, blanching, roasting, baking, frying, grilling, steaming, boiling, simmering, poaching, braising, stewing, sauteing, pressure cooking, sous vide, smoking, fermenting, freezing, and the like. A refreshment preparation style may be labeled 136 for an individual ingredient and/or a combination of one or more ingredients contained within a resource. For instance and without limitation, a resource such as a meal containing millet porridge with stewed apples and hazelnuts may contain a refreshment preparation style for the stewed apples, the hazelnuts, and the overall finished product of the millet porridge. In such an instance, the stewed apples may be prepared by peeling the apples, combining the apples in a large saucepan with sugar, lemon juice, and spices, cooking the apples over medium heat, and adjusting consistency to make the apples thicker if prepared. The hazelnuts may be prepared by roasting raw hazelnuts in an oven at 350 degrees Fahrenheit for 10-15 minutes. The millet porridge may be prepared by combining millet with water or broth and gently simmering on a stovetop for 15-20 minutes. The final product may be prepared by topping a serving of millet with the stewed apples and roasted hazelnuts.

With continued reference to FIG. 1, a "provider fulfillment score" as used in this disclosure, is any numerical and/or categorical rating system designed to evaluate the overall healthfulness and/or nutritional quality of a resource as prepared by a nourishment provider. A provider fulfillment score may be calculated based on one or more factors such as total energy content as indicated by total calories per serving; positive nutrients as indicated by quantities of nutrients such as protein, fiber, vitamins and minerals; negative nutrients as indicated by quantities of saturated fat, added sugars, sodium, trans fats, seed oils, and the like; ability of a resource to meet the nutrition needs and/or requirements of a user's biological extraction, and/or phenotypic cluster; how well a resource optimizes a user's nutritional needs; how well a resource meets any user provided instructions and/or food preferences; and the like. In an embodiment, a provider fulfillment score may contain a color-coded system whereby a color such as green may represent the healthiest option whereas a color such as red may represent the least healthiest option. In yet another non-limiting example a provider fulfillment score may contain a start rating system where five stars may represent the healthiest option whereas zero starts may represent the least healthiest option. In yet another non-limited example, a provider fulfillment score may contain a numerical system whereby a score such as 100 may represent the healthiest option whereas a score of 0 may represent the least healthiest option. For instance and without limitation, a request for a resource 108 may contain a request for a gluten free breakfast and a first nourishment provider 128 may be assigned a provider fulfillment score of 47 for a gluten free breakfast consisting of gluten free pancakes with maple syrup containing high fructose corn syrup and a side of bacon, whereas a second nourishment provider 140 may be assigned a provider fulfillment score of 79 for a gluten free breakfast consisting of organic Greek yogurt topped with blueberries, walnuts, and fresh local honey. In yet another non-limiting example, a request for a resource 108 may contain a request for a high fiber lunch option for a user with a genetic predisposition of colon cancer, and whereby a first nourishment provider 128 may be assigned a provider fulfillment score of 18 for a lunch containing a ham and cheese sandwich on a croissant containing a total of 3 grams of fiber, whereby a second nourishment provider 140 may be assigned a provider fulfillment score of 64 for a lunch containing a mesclun green salad topped with chicken salad, grapes, pumpkin seeds, and flax seeds containing a total of 12 grams of fiber. In an embodiment, provider fulfillment score may be generated using machine learning, including any machine learning process as described herein. Processor 104 generates resource guidance 148 as a function of a provider fulfillment score. For example, processor 104 may generate resource guidance 148 indicating selection of a nourishment provider with a provider fulfillment score of 92, with instructions for route guidance and delivery in lieu of selecting a nourishment provider with a provider fulfillment score of 27.

Figure 2:
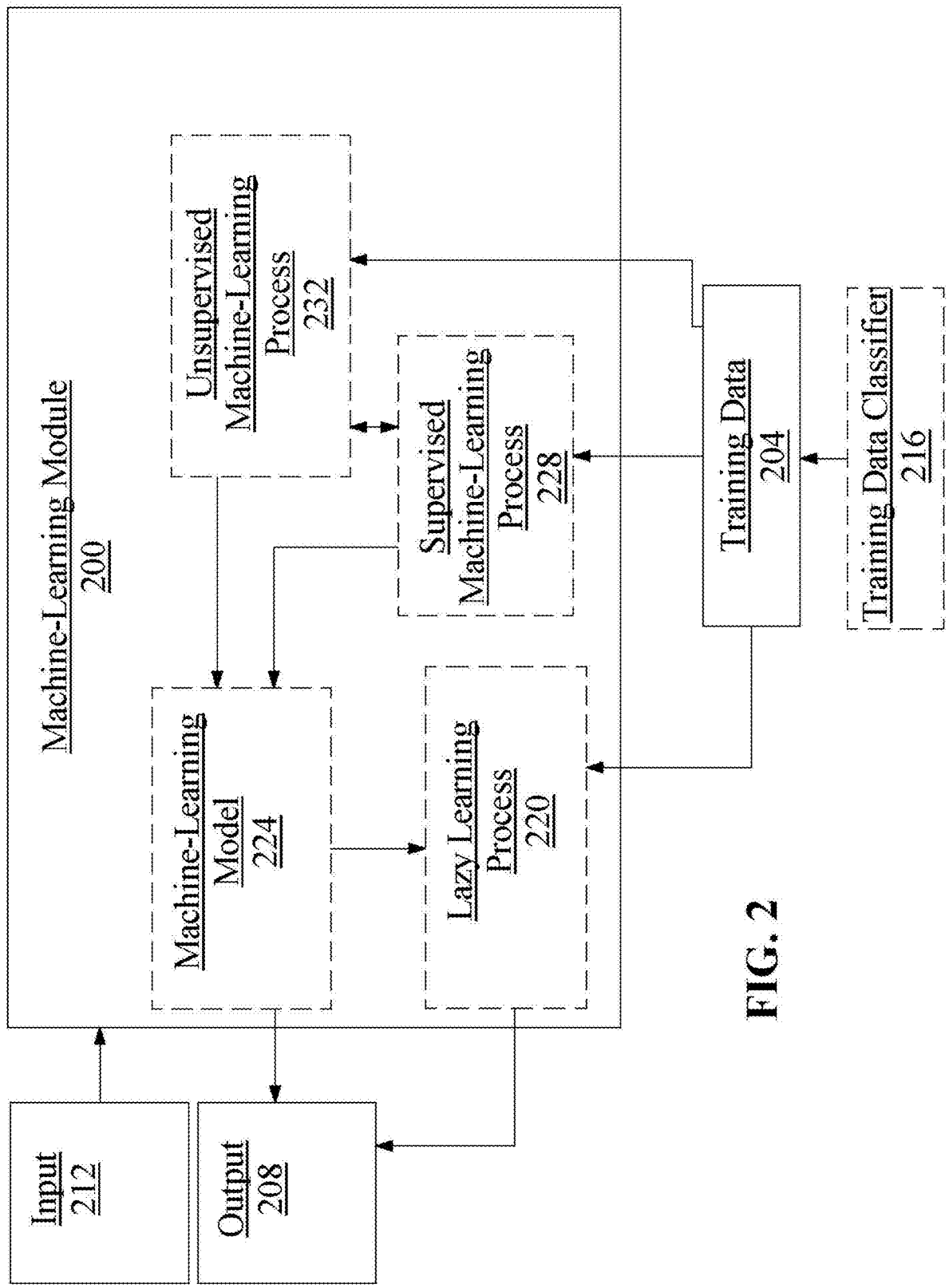
FIG. 2 is an illustration of an exemplary embodiment of a machine learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example inputs may include but are not limited to resource parameter 144, requests for a resource, nutrition plan 116, condition plan 120, desired allocation 112s, nourishment providers, depot label 156, resource guidance 148 and outputs may include resource guidance 148, nourishment providers, depot label 156 and the like.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or label 136 associated therewith. A classifier may be configured to output at least a datum that label 136 or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to sub-categories including but not limited to users with shared characteristics of biological extractions, phenotypic clusters, requests for resources, nourishment providers, desired allocation 112s, depot label 156, resource guidance 148, nutrition plan 116, condition plan 120, provider fulfillment scores, nourishment gaps and the like.

Still referring to FIG. 2, a computing device may be configured to generate a classifier using a Naïve Bayes classification algorithm. Naïve Bayes classification algorithm generates classifiers by assigning class label 136 to problem instances, represented as vectors of element values. Class label 136 are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B) = P(B/A) P(A) = P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification label 136. A computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, a computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein.

As a non-limiting example, an initial heuristic may include a ranking of associations between inputs and elements of training data. Heuristic may include selecting some number of highest-ranking associations and/or training data elements.

With continued reference to FIG. 2, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation 160 of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l = \sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor 104, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. A computing device, processor 104, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 2, computer, processor 104, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 2, computer, processor 104, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor 104, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor 104, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor 104, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor 104 may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor 104, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor 104, and/or module may use averaging, such as luma or chroma averaging in images, to fill in data units in between original data units.

In some embodiments, and with continued reference to FIG. 2, computing device, processor 104, and/or module may down-sample elements of a training example to a desired lower number of data elements. As a non-limiting example, a high pixel count image may have 256 pixels, however a desired number of pixels may be 128. Processor 104 may down-sample the high pixel count image to convert the 256 pixels into 128 pixels. In some embodiments, processor 104 may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 2, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 2, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max} : X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the 25$^{th}$ percentile value and the 50$^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 2, computing device, processor 104, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may inputs may include but are not limited to resource parameter 144, requests for a resource, nutrition plan 116, condition plan 120, desired allocation 112s, nourishment providers, depot label 156, resource guidance 148 and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor 104, and/or module may be configured to perform method, method step, sequence of method steps and/or algorithm described in reference to this figure, in any order and with any degree of repetition. For instance, a computing device, processor 104, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor 104, and/or module may perform any step, sequence of steps, or algorithm in parallel, such as simultaneously and/or substantially simultaneously performing a step two or more times using two or more parallel threads, processor 104 cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to label 136; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled 136 according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor 104 performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor 104, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

With continued reference to FIG. 2, machine learning process may include a generative machine learning process. As used in this disclosure, a "generative machine learning process" is a process that automatedly, using a prompt (i.e., input), generates an output consistent with training data; this is in contrast to a non-machine learning software program where outputs are determined in advance by a user and written in a programming language. In some embodiments, generative machine-learning processes may determine patterns and structures from training data and use these patterns and structures to synthesize new data with similar characteristics, as a function of an input. As a non-limiting example, generative machine-learning process may determine patterns and structures from training data of language processing models, augmentation machine-learning model, or any machine-learning models described in the entirety of this disclosure and may use these patterns to synthesize new data, augmented action data as a function of an input, such as but not limited to action data, external data, target data point, or the like.

With continued reference to FIG. 2 generative machine learning processes may synthesize data of different types or domains, including without limitation text, code, images, function data 112, functional signature 124, and/or optimized functional signature 128. Exemplary generative machine learning systems trained on words or word tokens, operant in text domain, include GPT-3, LaMDA, LLAMA, BLOOM, GPT-4, and the like. Exemplary machine learning processes trained on programming language text (i.e., code) include without limitation OpenAI Codex. Exemplary machine learning processes trained on sets of images (for instance with text captions) include Imagen, DALL-E, Midjourney, Adobe Firefly, Stable Diffusion, and the like; image generative machine learning processes, in some cases, may be trained for text-to-image generation and/or neural style transfer. Exemplary generative machine learning processes trained on molecular data include, without limitation, AlphaFold, which may be used for protein structure prediction and drug discovery. Generative machine learning processes trained on audio training data include MusicLM which may be trained on audio waveforms of music correlated with text annotations; music generative machine learning processes, in some cases, may generate new musical samples based on text descriptions. Exemplary generative machine learning processes trained on video include without limitation RunwayML and Make-A-Video by Meta Platforms. Finally, exemplary generative machine learning processes trained using robotic action data include without limitation UniPi from Google Research.

With continued reference to FIG. 2, in some cases a generative machine learning process may include a generative adversarial network (GAN). As used in this disclosure, a "generative adversarial network" is a machine learning process that includes at least two adverse networks configured to synthesize data according to prescribed rules (e.g., rules of a game). In some cases, a generative adversarial network may include a generative and a discriminative network, where the generative network generates candidate data and the discriminative network evaluates the candidate data. An exemplary GAN may be described according to a following game: Each probability space $(\Omega, \mu_{ref})$ defines a GAN game. There are two adverse networks: a generator network and a discriminator network. Generator network strategy set is $P(\Omega)$, the set of all probability measures $\mu_G$ on $\Omega$. Discriminator network strategy set is the set of Markov kernels $\mu_D: \Omega \rightarrow P[0,1]$, where $P[0,1]$ is set of probability measures on $[0,1]$. GAN game may be a zero-sum game, with objective function:

$$L(\mu_G, \mu_D) = \mathbb{E}_{x \sim \mu_{ref}, y \sim \mu_D(x)}[\ln y] + \mathbb{E}_{x \sim \mu_G, y \sim \mu_D(x)}[\ln(1-y)].$$

Generally, generator network may aim to minimize objective, and discriminator network may aim to maximize the objective. Specifically, generator network seeks to approach $\mu_G \approx \mu_{ref}$, said another way, generator network produces candidate data that matches its own output distribution as closely as possible to a reference distribution (provided with training data). Discriminator network outputs a value close to 1 when candidate data appears to be from reference (training data) distribution, and to output a value close to 0 when candidate data looks like it came from generator network distribution. Generally speaking, generative network generates candidates while discriminative network evaluates them, with contest operating in terms of data distributions. In some embodiments, generator network may learn to map from a latent space to a data distribution of interest, while discriminator network may distinguish candidates produced by the generator network from a true data distribution (e.g., training data). In some cases, generator network's training objective is to increase an error rate of discriminator network (i.e., "fool" the discriminator network by producing novel candidates that the discriminator thinks are not synthesized but, instead, are part of training data). In some cases, a known dataset may serve as initial training data for discriminator network. Training may involve presenting discriminator network with samples from training dataset until it achieves acceptable accuracy. In some cases, generator network may be trained on whether the generator network succeeds in fooling discriminator network. A generator network may be seeded with randomized input that is sampled from a predefined latent space (e.g. a multivariate normal distribution). Thereafter, candidates synthesized by generator network may be evaluated by discriminator network. Independent backpropagation procedures may be applied to both networks so that generator network may produce better samples, while discriminator network may become more skilled at flagging synthetic samples. When used for image generation, generator network may be a deconvolutional neural network, and discriminator may be a convolutional neural network.

Still referring to FIG. 2, may include a large language model (LLM). A "large language model," as used herein, is a deep learning data structure that can recognize, summarize, translate, predict and/or generate text and other content based on knowledge gained from massive datasets. Large language models may be trained on large sets of data. Training sets may be drawn from diverse sets of data such as, as non-limiting examples, novels, blog posts, articles, emails, unstructured data, electronic records, and the like. In some embodiments, training sets may include a variety of subject matters, such as, as nonlimiting examples, medical report documents, electronic condition records, entity documents, business documents, inventory documentation, emails, user communications, function data 112, temporal elements, functional signature 124, optimized functional signature 128 and the like. In some embodiments, training sets of an LLM may include information from one or more public or private databases. As a non-limiting example, training sets may include databases associated with an entity. In some embodiments, training sets may include portions of documents associated with the electronic records correlated to examples of outputs. In an embodiment, an LLM may include one or more architectures based on capability requirements of an LLM. Exemplary architectures may include, without limitation, GPT (Generative Pretrained Transformer), BERT (Bidirectional Encoder Representations from Transformers), T5 (Text-To-Text Transfer Transformer), and the like. Architecture choice may depend on a needed capability such generative, contextual, or other specific capabilities.

With continued reference to FIG. 2, in some embodiments, an LLM may be generally trained. As used in this disclosure, a "generally trained" LLM is an LLM that is trained on a general training set comprising a variety of subject matters, data sets, and fields. In some embodiments, an LLM may be initially generally trained. Additionally, or alternatively, an LLM may be specifically trained. As used in this disclosure, a "specifically trained" LLM is an LLM that is trained on a specific training set, wherein the specific training set includes data including specific correlations for the LLM to learn. As a non-limiting example, an LLM may be generally trained on a general training set, then specifically trained on a specific training set. In an embodiment, specific training of an LLM may be performed using a supervised machine learning process. In some embodiments, generally training an LLM may be performed using an unsupervised machine learning process. As a non-limiting example, specific training set may include information from a database. As a non-limiting example, specific training set may include text related to the users such as user specific data for electronic records correlated to examples of outputs. In an embodiment, training one or more machine learning models may include setting the parameters of the one or more models (weights and biases) either randomly or using a pretrained model. Generally training one or more machine learning models on a large corpus of text data can provide a starting point for fine-tuning on a specific task. A model such as an LLM may learn by adjusting its parameters during the training process to minimize a defined loss function, which measures the difference between predicted outputs and ground truth. Once a model has been generally trained, the model may then be specifically trained to fine-tune the pretrained model on task-specific data to adapt it to the target task. Fine-tuning may involve training a model with task-specific training data, adjusting the model's weights to optimize performance for the particular task. In some cases, this may include optimizing the model's performance by fine-tuning hyperparameters such as learning rate, batch size, and regularization. Hyperparameter tuning may help in achieving the best performance and convergence during training. In an embodiment, fine-tuning a pretrained model such as an LLM may include fine-tuning the pretrained model using Low-Rank Adaptation (LoRA). As used in this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

With continued reference to FIG. 2, in some embodiments an LLM may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. An LLM may include a text prediction based algorithm configured to receive an article and apply a probability distribution to the words already typed in a sentence to work out the most likely word to come next in augmented articles. For example, if some words that have already been typed are "Nice to meet", then it may be highly likely that the word "you" will come next. An LLM may output such predictions by ranking words by likelihood or a prompt parameter. For the example given above, an LLM may score "you" as the most likely, "your" as the next most likely, "his" or "her" next, and the like. An LLM may include an encoder component and a decoder component.

Still referring to FIG. 2, an LLM may include a transformer architecture. In some embodiments, encoder component of an LLM may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 2, an LLM and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

With continued reference to FIG. 2, attention mechanism may represent an improvement over a limitation of an encoder-decoder model. An encoder-decider model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, an LLM may predict the next word by searching for a set of positions in a source sentence where the most relevant information is concentrated. An LLM may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

Still referring to FIG. 2, attention mechanism may include, without limitation, generalized attention self-attention, multi-head attention, additive attention, global attention, and the like. In generalized attention, when a sequence of words or an image is fed to an LLM, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, an LLM may pick up particular parts at different positions in the input sequence and over time compute an initial composition of the output sequence. In multi-head attention, an LLM may include a transformer model of an attention mechanism. Attention mechanisms, as described above, may provide context for any position in the input sequence. For example, if the input data is a natural language sentence, the transformer does not have to process one word at a time. In multi-head attention, computations by an LLM may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), an LLM may make use of attention alignment scores based on a number of factors. Alignment scores may be calculated at different points in a neural network, and/or at different stages represented by discrete neural networks. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, an LLM may either attend to all source words or predict the target sentence, thereby attending to a smaller subset of words.

With continued reference to FIG. 2, multi-headed attention in encoder may apply a specific attention mechanism called self-attention. Self-attention allows models such as an LLM or components thereof to associate each word in the input, to other words. As a non-limiting example, an LLM may learn to associate the word "you", with "how" and "are". It's also possible that an LLM learns that words structured in this pattern are typically a question and to respond appropriately. In some embodiments, to achieve self-attention, input may be fed into three distinct fully connected neural network layers to create query, key, and value vectors. A query vector may include an entity's learned representation for comparison to determine attention score. A key vector may include an entity's learned representation for determining the entity's relevance and attention weight. A value vector may include data used to generate output representations. Query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

Still referencing FIG. 2, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 2, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

Continuing to refer to FIG. 2, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With further reference to FIG. 2, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 2, first multi-headed attention layer may be configured to not condition to future tokens. As a non-limiting example, when computing attention scores on the word "am," decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "0" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens."

Still referring to FIG. 2, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 2, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word.

Still referring to FIG. 2, decoder may take this output and add it to the decoder inputs. Decoder may continue decoding until a token is predicted. Decoder may stop decoding once it predicts an end token.

Continuing to refer to FIG. 2, in some embodiment, decoder may be stacked N layers high, with each layer taking in inputs from the encoder and layers before it. Stacking layers may allow an LLM to learn to extract and focus on different combinations of attention from its attention heads.

With continued reference to FIG. 2, an LLM may receive an input. Input may include a string of one or more characters. Inputs may additionally include unstructured data. For example, input may include one or more words, a sentence, a paragraph, a thought, a query, and the like. A "query" for the purposes of the disclosure is a string of characters that poses a question. In some embodiments, input may be received from a user device. User device may be any computing device that is used by a user. As non-limiting examples, user device may include desktops, laptops, smartphones, tablets, and the like. In some embodiments, input may include any set of data associated with vitality profile 108, function data 112, temporal elements, functional signature 124, and/or optimized functional signature 128.

With continued reference to FIG. 2, an LLM may generate at least one annotation as an output. At least one annotation may be any annotation as described herein. In some embodiments, an LLM may include multiple sets of transformer architecture as described above. Output may include a textual output. A "textual output," for the purposes of this disclosure is an output comprising a string of one or more characters. Textual output may include, for example, a plurality of annotations for unstructured data. In some embodiments, textual output may include a phrase or sentence identifying the status of a user query. In some embodiments, textual output may include a sentence or plurality of sentences describing a response to a user query. As a non-limiting example, this may include restrictions, timing, advice, dangers, benefits, and the like.

Figure 3:
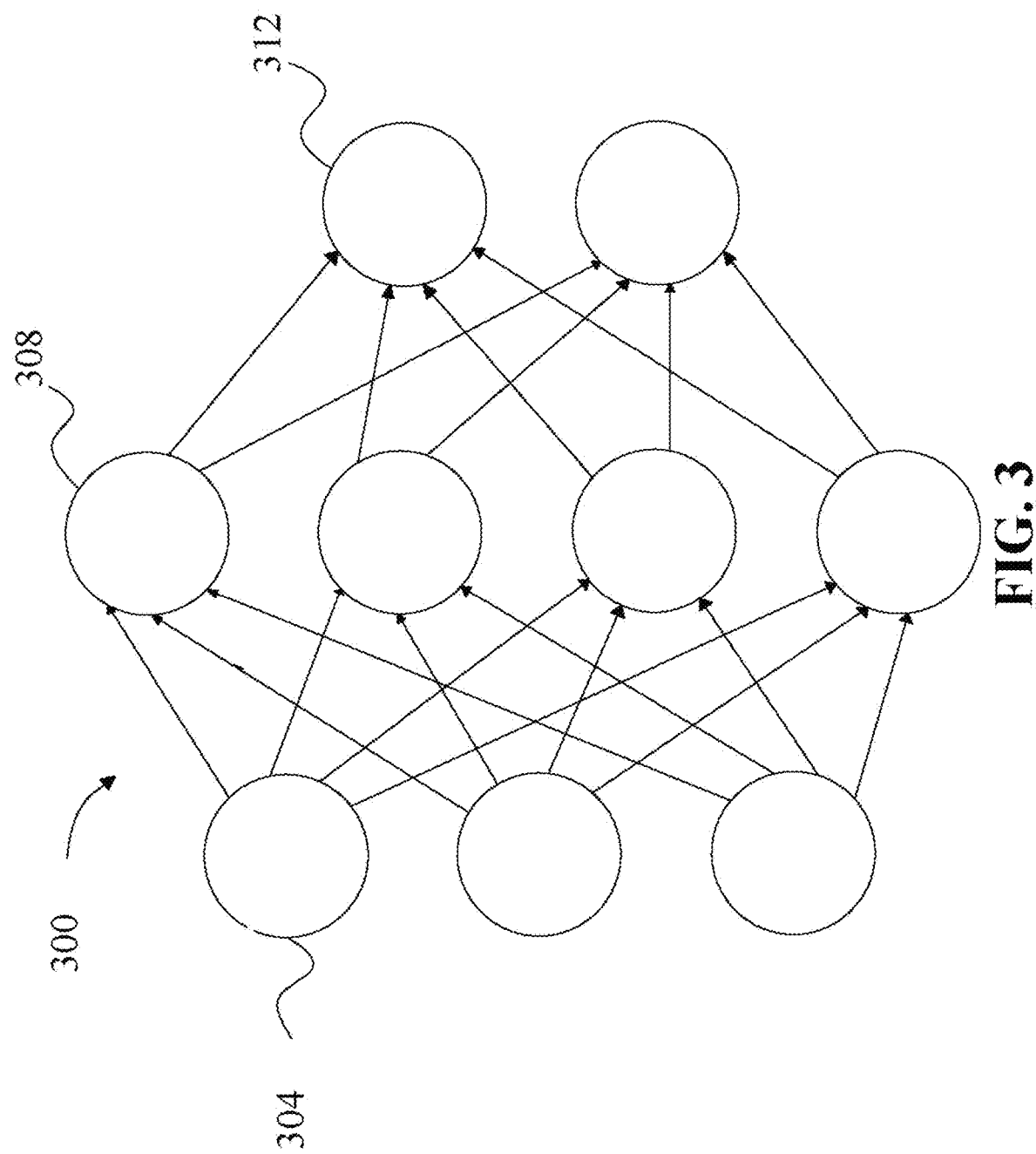
FIG. 3 is an illustration of an exemplary embodiment of a neural network.

Referring now to FIG. 3, an exemplary embodiment of neural network 3 is illustrated. A neural network 3 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 4:
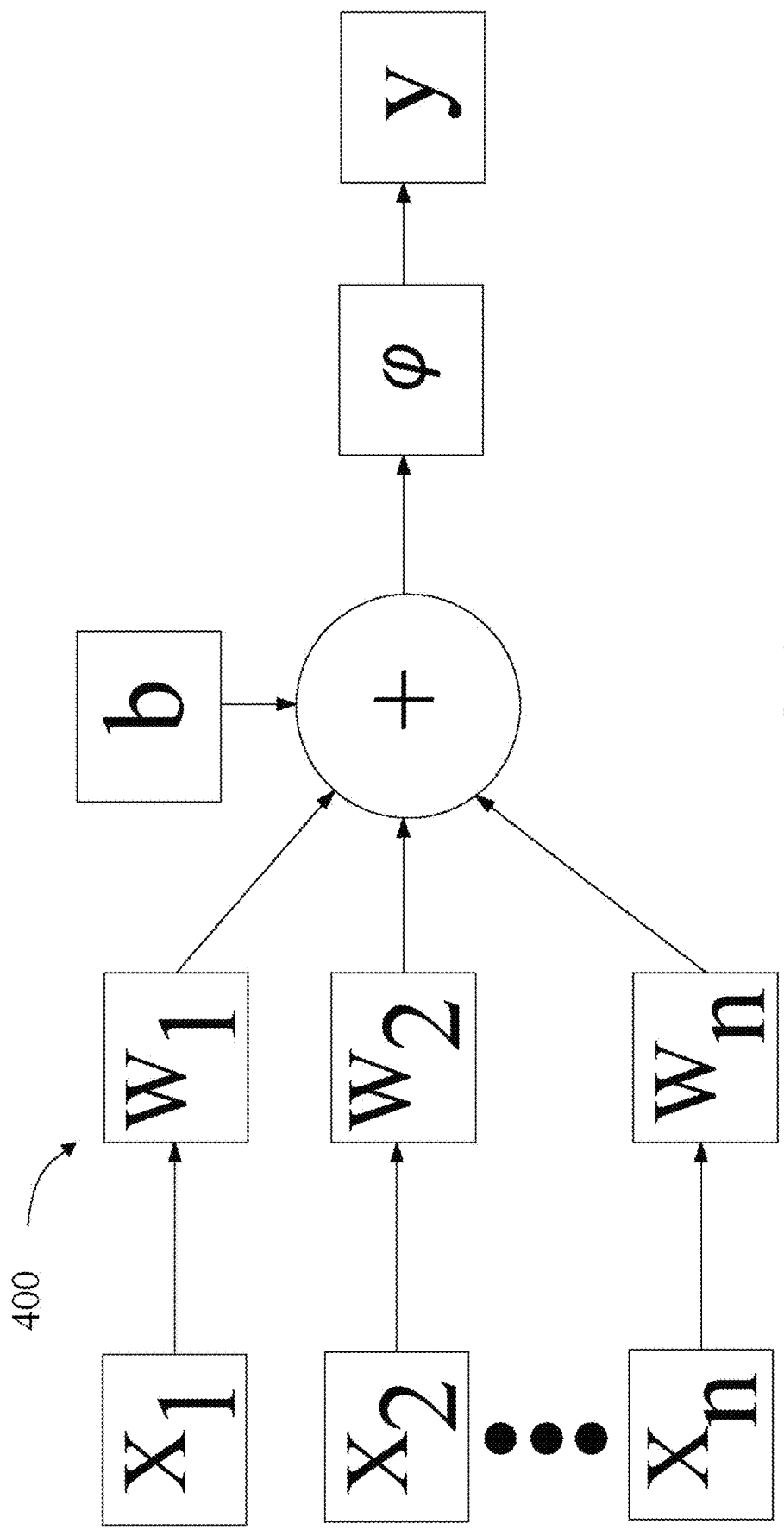
FIG. 4 is an illustration of an exemplary embodiment of a node.

Referring now to FIG. 4, an exemplary embodiment of a node 400 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1-e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax,x)$ for some a, an exponential linear units function such as $$f(x) = \begin{cases} x & \text{for } x \geq 0 \\ \alpha(e^x - 1) & \text{for } x < 0 \end{cases}$$

for some value of a (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 5:
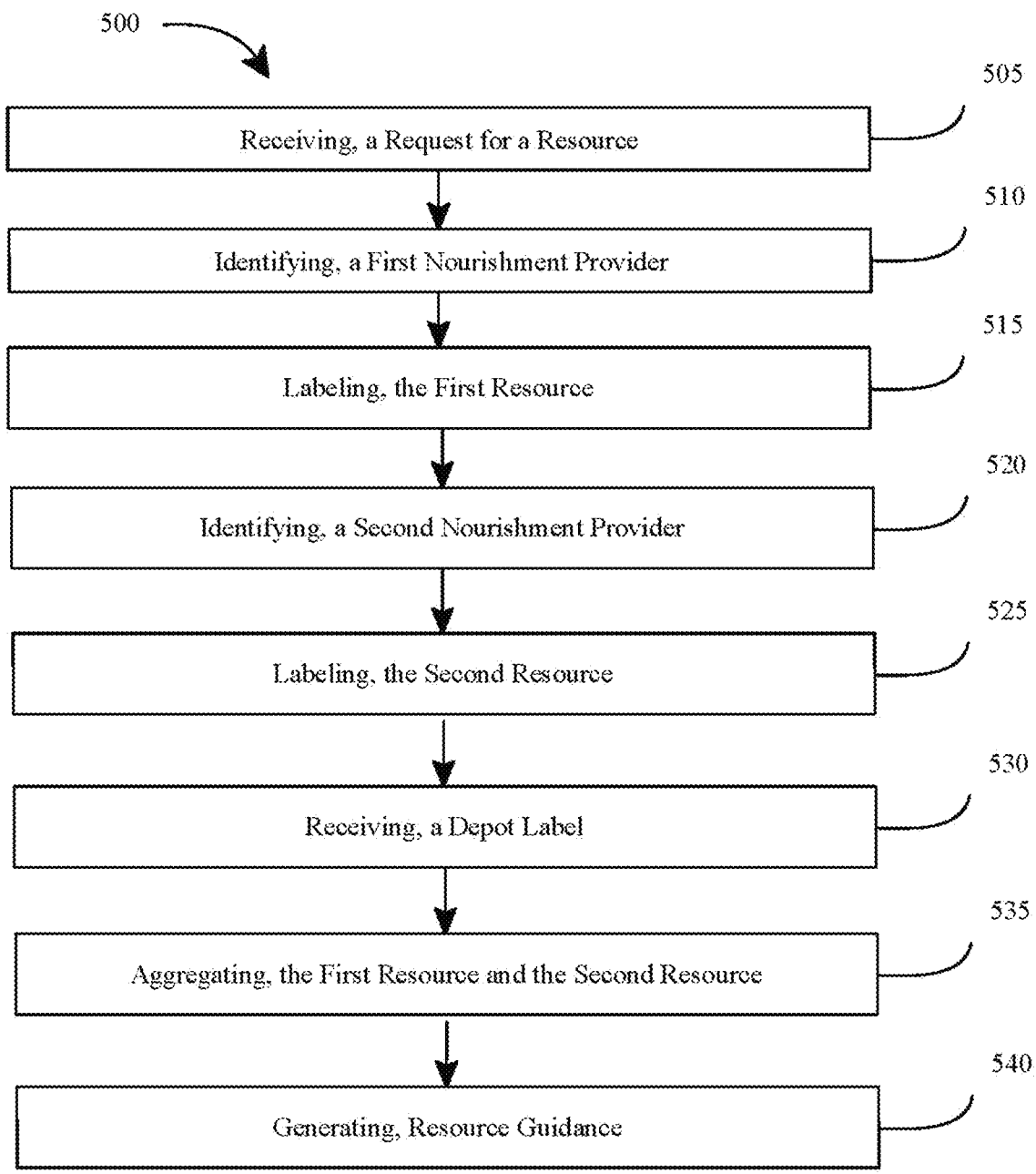
FIG. 5 is an illustration of an exemplary embodiment of a flow diagram of a method for resource guidance.

Referring now to FIG. 5, an exemplary embodiment 500 of a method for resource guidance 148 is illustrated. At step 505, processor 104 receives a request for a resource 108 containing a desired allocation 112. A request for a resource 108 includes any request for a resource 108 as described above in more detail in reference to FIGS. 1-4. A desired allocation 112 includes any desired allocation 112 as described above in more detail in reference to FIGS. 1-4.

With continued reference to FIG. 5, at step 510, processor 104 identifies by the at least processor 104 a first nourishment provider 128 for a first resource. A nourishment provider includes any nourishment provider as described above in more detail in reference to FIGS. 1-4. A first resource includes any resource as described above in more detail in reference to FIGS. 1-4. A resource may include an edible, including for example any meal and/or snack option as described above. A resource may include a product, such as for example household items including laundry detergent or a beverage such as bottles of water. In yet another non-limiting example, a resource may include a cosmetic product such as hairspray, shampoo, and/or facewash.

With continued reference to FIG. 5, at step 515, processor 104 label 136 the first resource as a function of a desired allocation 112. Labeling 136, the first resource as a function of a desired allocation 112 may be performed utilizing any methodology as described above in more detail in reference to FIGS. 1-4.

With continued reference to FIG. 5, at step 520, processor 104 identifies a second nourishment provider 140 for a second resource. Identifying the second nourishment provider 140 may be performed utilizing any methodology as described above in more detail in reference to FIGS. 1-4. In an embodiment, the first resource provider may be different than the second resource provider. In yet another non-limiting example, the first resource provider may be the same as the second resource provider.

With continued reference to FIG. 5, at step 525, processor 104 label 136 the second resource as a function of the first nourishment resource and the desired allocation 112. This may be performed utilizing any methodology as described above in more detail in reference to FIGS. 1-4.

With continued reference to FIG. 5, at step 530, processor 104 receives a depot label 156 from the first nourishment provider 128 and the second nourishment provider 140. Depot label 156 includes any depot label 156 as described above in more detail in reference to FIGS. 1-4.

With continued reference to FIG. 5, at step 535, processor 104 aggregates the first resource and the second resource as a function of the depot label 156. Aggregation 160 may be performed utilizing any methodology as described above in more detail in reference to FIGS. 1-4.

With continued reference to FIG. 5, at step 540, processor 104 generates resource guidance 148 using the depot label 156. This may be performed utilizing any methodology as described above in more detail in reference to FIGS. 1-4.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
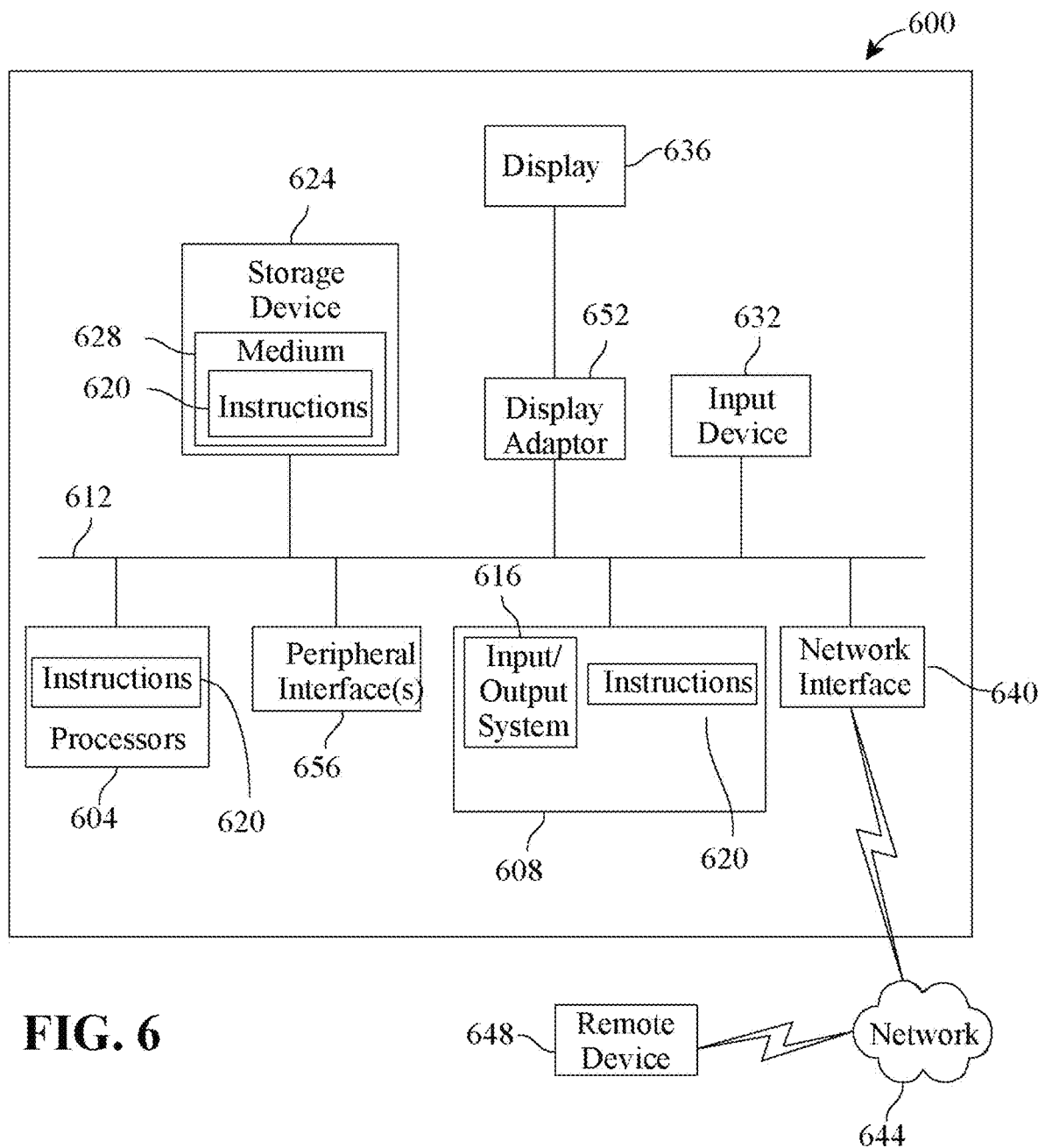
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor 104, such as without limitation a processor 104 incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor 104, digital signal processor 104 (DSP), Field Programmable Gate Array (FPGA), Complex Programmable Logic Device (CPLD), Graphical Processing Unit (GPU), general purpose GPU, Tensor Processing Unit (TPU), analog or mixed signal processor 104, Trusted Platform Module (TPM), a floating point unit (FPU), system on module (SOM), and/or system on a chip (SoC).

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for resource guidance, wherein the apparatus comprises:
   at least a processor; and
   a memory communicatively connected to the at least a processor, wherein the memory containing instructions configuring the at least a processor to:
   receive a request for a resource containing a desired allocation;
   identify a first nourishment provider for a first resource;
      label the first resource as a function of the desired allocation, wherein labeling the first resource utilizes a machine learning model which comprises:
         receiving a resource parameter for the first nourishment provider;
         receiving training data, wherein the intervention training data correlates a plurality of resource parameter data to a plurality of resource guidance data;
         iteratively training the machine learning model with the training data and includes retraining the machine learning model with feedback from previous iterations of the machine learning model;
         computing resource guidance as a function of the resource parameter and the trained machine learning model;
   identify a second nourishment provider for a second resource;
   label the second resource as a function of the first nourishment resource and the desired allocation;
   receive a depot label from the first nourishment provider and the second nourishment provider;
   aggregate the first resource and the second resource as a function of the depot label; and
   generate resource guidance using the depot label.

2. The apparatus of claim 1, wherein the desired allocation further comprises a nutrition plan.

3. The apparatus of claim 1, wherein the desired allocation further comprises a condition plan.

4. The apparatus of claim 1, wherein the desired allocation further comprises a timestamp.

5. The apparatus of claim 1, wherein identifying the first nourishment provider further comprises:
   parsing, the request for a resource to identify a nourishment demand;
   identifying a resource relating to the nourishment demand;
   locating, the first nourishment provider using the nourishment demand and the resource.

6. The apparatus of claim 1, wherein generating resource guidance further comprises:
   identifying a constraint within the resource guidance; and
   updating the resource guidance as a function of the constraint.

7. The apparatus of claim 1 further comprising:
   locating a nourishment gap associated with the first nourishment provider; and
   identifying a third nourishment provider for the nourishment gap.

8. The apparatus of claim 1, wherein identifying the first nourishment provider further comprises:
   determining a resource metric between the first nourishment provider and a depot; and
   selecting the first nourishment provider as a function of the resource metric.

9. The apparatus of claim 1, wherein aggregating the first resource and the second resource further comprises:
   reviewing the first resource and the second resource;
   calculating a provider fulfillment score for the first resource and the second resource as a function of the desired allocation and the reviewed first resource and the reviewed second resource; and
   generating resource guidance as a function of the provider fulfillment score.

10. A method for resource guidance, the method comprising:
    receiving, by at least a processor, a request for a resource containing a desired allocation;
    identifying, by the at least a processor, a first nourishment provider for a first resource;
       labeling, by the at least a processor, the first resource as a function of the desired allocation, wherein labeling the first resource utilizes a machine learning model which comprises:
          receiving a resource parameter for the first nourishment provider;
          receiving training data, wherein the intervention training data correlates a plurality of resource parameter data to a plurality of resource guidance data;
          iteratively training the machine learning model with the training data and includes retraining the machine learning model with feedback from previous iterations of the machine learning model;
          computing resource guidance as a function of the resource parameter and the trained machine learning model;
    identifying, by the at least a processor, a second nourishment provider for a second resource;
    labeling, by the at least a processor, the second resource as a function of the first nourishment resource and the desired allocation;
    receiving, by the at least a processor, a depot label from the first nourishment provider and the second nourishment provider;
    aggregating, by the at least a processor, the first resource and the second resource as a function of the depot label; and
    generating, by the at least a processor, resource guidance using the depot label.

11. The method of claim 10, wherein the desired allocation further comprises a nutrition plan.

12. The method of claim 10, wherein the desired allocation further comprises a condition plan.

13. The method of claim 10, wherein the desired allocation further comprises a timestamp.

14. The method of claim 10, wherein identifying the first nourishment provider further comprises:
    parsing, the request for a resource to identify a nourishment demand;
    identifying a resource relating to the nourishment demand;
    locating, the first nourishment provider using the nourishment demand and the resource.

15. The method of claim 10, wherein generating resource guidance further comprises:
    identifying a constraint within the resource guidance; and
    updating the resource guidance as a function of the constraint.

16. The method of claim 10 further comprising:
    locating a nourishment gap associated with the first nourishment provider; and identifying a third nourishment provider for the nourishment gap.

17. The method of claim 10, wherein identifying the first nourishment provider further comprises:
   determining a resource metric between the first nourishment provider and a depot; and
   selecting the first nourishment provider as a function of the resource metric.

18. The method of claim 10, wherein aggregating the first resource and the second resource further comprises:
   reviewing the first resource and the second resource;
   calculating a provider fulfillment score for the first resource and the second resource as a function of the desired allocation and the reviewed first resource and the reviewed second resource; and
   generating resource guidance as a function of the provider fulfillment score.

\* \* \* \* \*